United States Patent [19]

Reuther

[11] Patent Number: Plant 7,121

[45] Date of Patent: Jan. 23, 1990

[54] KOHLERIA NAMED ORANGEGLOW

[75] Inventor: Gerhard Reuther, Geisenheim, Fed. Rep. of Germany

[73] Assignee: Scipla Trust, Liechtenstein

[21] Appl. No.: 273,401

[22] Filed: Nov. 18, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A cultivar of Kohleria plant named Orangeglow having compact growth, early flowering characteristics, orange-red corolla tube and rounded corolla limbs, and by its floriferous habit.

3 Drawing Sheets

The present invention comprises a new and distinct cultivar of *Gesneriaceac kohleria,* hereinafter referred to by the cultivar name Orangeglow.

Orangeglow originated by me through mutagenesis using NMH (N-nitroso-N-methyl urea) as the mutagen applied to Kohleria plants which may be identified as '*Kohleria amabilis*×*Kohleria bogotensis*×*Kohleria eriantha', in Geisenheim, West Germany. The first mutagenic treatment was performed Dec.* 5, 1979, and the second treatment was performed June 23, 1982. The new cultivar was selected from the plants subjected to such treatments.

The first act of asexual reproduction of Orangeglow was accomplished by me using standard tissue culture reproduction practice in Geisenheim, West Germany. Horticultural examination of selected units has demonstrated that the combination of characteristics as herein disclosed for Orangeglow are firmly fixed and are retained through successive generations of asexual reproduction.

Orangeglow has not been observed under all possible environmental conditions. The phenotype may vary significantly with variations in environment such as temperature, light intensity and day length. The following observations, measurements and comparisons describe plants asexually reproduced by tissue culture practices and grown in Geisenheim, West Germany under greenhouse conditions which approximate those generally used in commercial practice. Unless otherwise noted, color references used herein are made to The Royal Horticultural Society Colour Chart (RHS). Where reference is made to "HCC" color values, The Horticultural Colour Chart issued by the British Colour Council is intended.

The accompanying photographic drawings show typical specimen plants and flowers of the new cultivar. The colors therein are reasonably true as possible for color illustrations of this type. In the drawings:

FIG. 1 is an illustration of a potted plant of Orangeglow showing habit of growth;

FIG. 2 is an illustration of a flower cluster of Orangeglow; and

FIG. 3 is a close-up illustration of an Orangeglow flower.

Orangeglow is particularly characterized by its compact plant growth habit, being approximately 50% of the plant height and leaf size of its parent. It also possesses early flowering characteristics, being up to seven weeks earlier than its parent when grown in a greenhouse under natural light conditions in winter at 50° N latitude.

PLANT

The plants grow upright; one or two shoots may originate from a single tissue culture-derived microcutting. At full blossoming and when grown in 10 cm conical containers, the plants are about 25 to 30-cm in height and about 20 to 25 cm in diameter.

The time required from transfer to soil until flowering is about 29 weeks; there is no significant influence of the season. Once started, flowering has been observed to continue for more than six months. Individual flowers last about three to five weeks under indoor conditions.

FOLIAGE

At full bloom, plants possess about 10 to 13 nodes, each bearing two opposite leaves of lanceolate shape with serrate margin. The oldest leaves are up to 13 cm long (excluding the petiole) and up to 5.5 cm wide; the petiole is up to 2 cm long. The relatively firm leaves generally possess seven main veins on either side of the midrib. Leaves and stems are pilose with colorless and red hairs. The top size of the leaves is Ivy Green HCC 1060/1–3, while the underside as well as stem and petioles show a reddish tone closest to Garnet Brown HCC 918/3.

FLOWER

The slightly zygomorphic tubular flowers are about 4 cm long with five rounded corolla limbs forming a circle of about 2 to 2.5 cm in diameter at the tip of the flower; the tube diameter varies from about 0.7 cm at the base to about 1.2 cm in the middle and about 1 cm at the distal end. The reproductive organs do not protrude out of the corolla tube. The outer surface of the corolla tube is pilose with red hairs, the margin and inner surface of the limbs bear glandular hairs. The peduncles and the 1 cm long calyx are green and pilose with red hairs. The flowers are arranged in inflorescences originating from the leaf axils of the upper nodes. Individual inflorescences may bear up to 10 or more flowers. More than 25 open flowers per plant at a time is not unusual. All the buds open, and there is no dropping of buds. The color of the corolla tube is Dutch Vermillion HCC 717 (RHS 40A), with lighter and more yellowish tone on the underside. The corolla limbs on the interior show dark red spots on a yellowish background, giving an overall impression of Signal Red HCC 719 (RSH 43A).

Orangeglow is sterile, similar to its parent. No viable pollen is formed.

PROPAGATION

The preferred method of propagation is by tissue culture; conventional tip cuttings give rise to less uniform stocks. The description given herein pertain to plants grown from tissue culture.

I claim:

1. A new and distinct cultivar of Kohleria plant named Orangeglow, as shown and described.

* * * * *

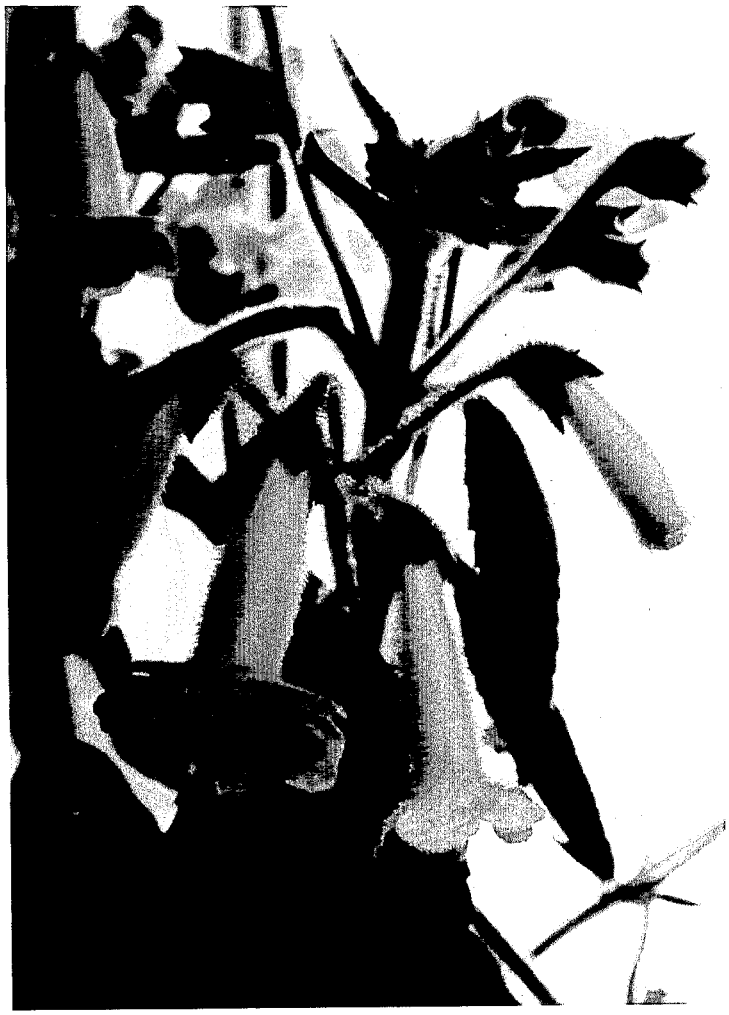

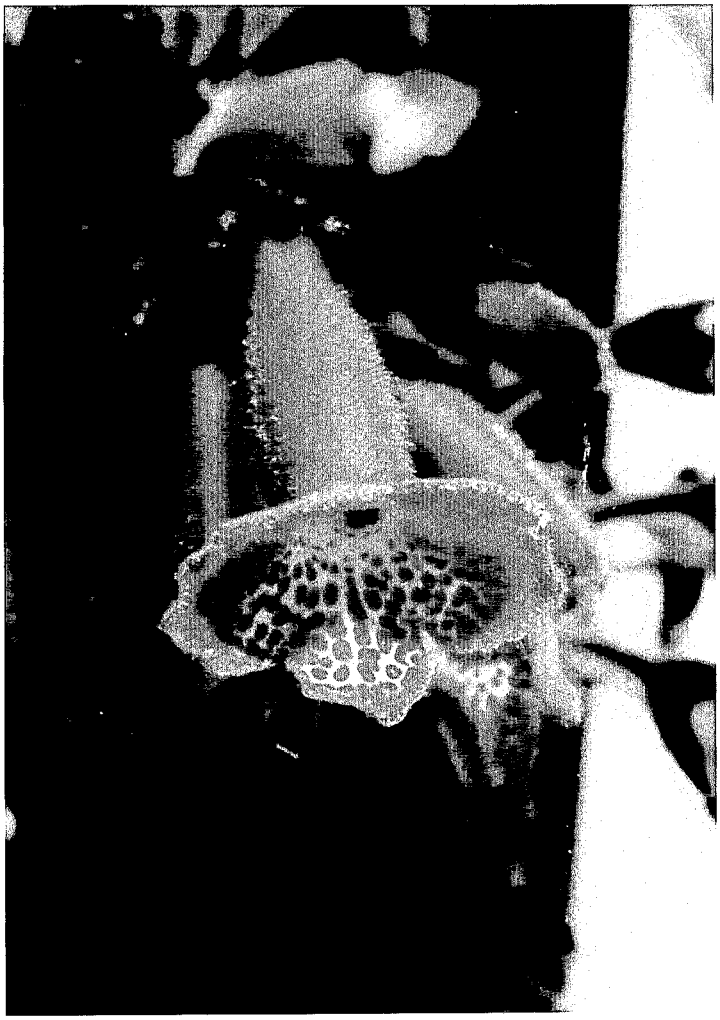

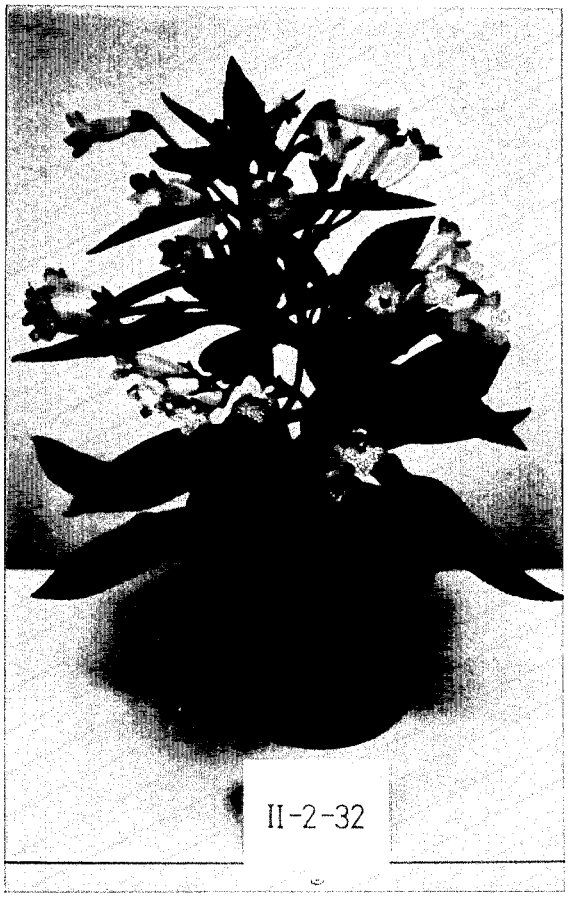
II-2-32